(12) United States Patent
Kitahara

(10) Patent No.: US 7,920,381 B2
(45) Date of Patent: Apr. 5, 2011

(54) INTERIOR COOLING STRUCTURE AND ULTRASOUND IMAGING APPARATUS

(75) Inventor: Toshihiro Kitahara, Tachikawa (JP)

(73) Assignee: Olympus Medical Systems Corp., Tokyo (JP)

( * ) Notice: Subject to any disclaimer, the term of this patent is extended or adjusted under 35 U.S.C. 154(b) by 69 days.

(21) Appl. No.: 12/504,160

(22) Filed: Jul. 16, 2009

(65) Prior Publication Data

US 2010/0014250 A1    Jan. 21, 2010

(30) Foreign Application Priority Data

Jul. 17, 2008  (JP) ................................ 2008-186309

(51) Int. Cl.
    *H05K 7/20*    (2006.01)
(52) U.S. Cl. .............. 361/695; 361/679.48; 361/679.49; 361/679.5; 361/890; 361/692; 165/104.33; 165/122; 454/184
(58) Field of Classification Search ............. 361/679.46, 361/679.48, 679.49, 679.5, 690–697, 715–724, 361/736, 752, 802, 816, 818, 831; 165/80.3, 165/80.4, 80.5, 104.33, 104.34, 121–126, 165/185; 174/16.1, 16.3, 252, 260; 312/223.2, 312/223.3, 236; 62/259.2
See application file for complete search history.

(56) References Cited

U.S. PATENT DOCUMENTS

| | | | | |
|---|---|---|---|---|
| 5,063,477 A | * | 11/1991 | Paggen et al. | 361/695 |
| 5,446,619 A | * | 8/1995 | Madsen et al. | 361/695 |
| 5,796,580 A | * | 8/1998 | Komatsu et al. | 361/679.48 |
| 5,813,243 A | * | 9/1998 | Johnson et al. | 62/259.2 |
| 5,860,291 A | * | 1/1999 | Johnson et al. | 62/259.2 |
| 5,923,531 A | * | 7/1999 | Bachman et al. | 361/690 |
| 6,034,870 A | * | 3/2000 | Osborn et al. | 361/690 |
| 6,061,237 A | * | 5/2000 | Sands et al. | 361/695 |
| 6,198,628 B1 | * | 3/2001 | Smith | 361/695 |
| 6,222,729 B1 | * | 4/2001 | Yoshikawa | 361/695 |
| 6,359,779 B1 | | 3/2002 | Frank, Jr. et al. | |
| 6,400,567 B1 | * | 6/2002 | McKeen et al. | 361/695 |

(Continued)

FOREIGN PATENT DOCUMENTS

EP    1 976 359 A2    10/2008

(Continued)

OTHER PUBLICATIONS

Extended European Search Report dated Sep. 24, 2009.

*Primary Examiner* — Michael V Datskovskiy
(74) *Attorney, Agent, or Firm* — Scully, Scott, Murphy & Presser, P.C.

(57) ABSTRACT

An interior cooling structure according to the present invention includes a frame in which a plurality of circuit board modules are stacked, with electronic components mounted on the plurality of circuit board modules by being classified by function; an external housing which covers the frame together with the plurality of circuit board modules; a plurality of cooling devices which reduce temperature rises in the external housing caused by heat produced by the plurality of circuit board modules; and a heat generating region a partitioned in such away as to enclose a circuit board module which has the highest total power consumption out of the plurality of circuit board modules, wherein the plurality of cooling devices are arranged in such away as to reduce temperature rises in the heat generating region by displaying capacity higher than capacity of each of the cooling devices.

21 Claims, 12 Drawing Sheets

U.S. PATENT DOCUMENTS

| | | | |
|---|---|---|---|
| 6,459,579 B1 * | 10/2002 | Farmer et al. | 361/695 |
| 6,504,718 B2 * | 1/2003 | Wu | 361/695 |
| 6,544,311 B1 * | 4/2003 | Walton et al. | 55/385.6 |
| 6,567,271 B2 * | 5/2003 | Stone et al. | 361/724 |
| 6,597,569 B1 * | 7/2003 | Unrein | 361/679.4 |
| 6,795,314 B1 * | 9/2004 | Arbogast et al. | 361/695 |
| 6,888,725 B2 * | 5/2005 | Kubo et al. | 361/719 |
| 6,972,953 B1 * | 12/2005 | Heirich et al. | 361/679.46 |
| 7,035,102 B2 * | 4/2006 | Holmes et al. | 361/695 |
| 7,036,027 B2 * | 4/2006 | Kim et al. | 713/300 |
| 7,046,470 B2 * | 5/2006 | Yamanashi et al. | 360/69 |
| 7,061,761 B2 * | 6/2006 | Tucker et al. | 361/695 |
| 7,154,148 B2 * | 12/2006 | Yamazaki et al. | 257/347 |
| 7,248,476 B2 * | 7/2007 | Holmes et al. | 361/695 |
| 7,352,571 B2 * | 4/2008 | Suzuki et al. | 361/679.48 |
| 7,426,111 B2 * | 9/2008 | Sonobe et al. | 361/695 |
| 7,466,547 B2 * | 12/2008 | Holmes et al. | 361/695 |
| 7,684,192 B2 * | 3/2010 | Holmes et al. | 361/695 |
| 7,706,141 B2 * | 4/2010 | Besold et al. | 361/690 |
| 7,706,142 B2 * | 4/2010 | Noisternig et al. | 361/695 |
| 7,733,649 B2 * | 6/2010 | Anderl et al. | 361/695 |
| 2002/0122296 A1 | 9/2002 | Stone et al. | |

FOREIGN PATENT DOCUMENTS

| | | |
|---|---|---|
| JP | 2001-340337 | 12/2001 |
| JP | 2006-020755 | 1/2006 |
| JP | 2006-156871 A | 6/2006 |
| JP | 2006-202869 | 8/2006 |

* cited by examiner

INTERIOR COOLING STRUCTURE AND ULTRASOUND IMAGING APPARATUS

CROSS REFERENCE TO RELATED APPLICATION

This application claims benefit of Japanese Application No. 2008-186309 filed in Japan on Jul. 17, 2008 the contents of which are incorporated by this reference.

BACKGROUND OF THE INVENTION

1. Field of the Invention

The present invention relates to an interior cooling structure which incorporates multiple circuit boards and, in particular, to an ultrasound imaging apparatus equipped with the interior cooling structure and connected to an ultrasound endoscope.

2. Description of the Related Art

In recent years, an ultrasound diagnostic method has spread widely. The ultrasound diagnostic method makes a diagnosis by emitting ultrasound into a body cavity and producing images of body conditions based on echo signals from the body cavity. Medical apparatus used for such ultrasound diagnostic method include, for example, an ultrasound echo apparatus which can produce images of conditions inside the body from the surface of the body and an ultrasound endoscope which includes, in its distal end portion, an ultrasound vibration unit that transmits/receives ultrasound can produce images of conditions inside the body by being inserted into a body cavity.

The ultrasound endoscope is connected with an ultrasound imaging apparatus (also called an ultrasound diagnostic apparatus) such as described, for example, in Japanese Patent Application Laid-Open Publication No. 2001-340337, where the ultrasound imaging apparatus is a medical apparatus which converts echo signals into images. As is well known, the ultrasound imaging apparatus contains multiple electronic components in a box-shaped housing. The housing contains multiple boards with various electronic components classified according to functional configuration of circuits.

Normally, a radiator fan (blower) and exhaust fan are installed in the apparatus housing to reduce temperature rises in the apparatus caused by heat produced by the electronic components mounted on the boards. Cooling configurations for use to reduce such temperature rises in apparatus are proposed, for example, in Japanese Patent Application Laid-Open Publication Nos. 2006-20755 and 2006-202869.

Japanese Patent Application Laid-Open Publication No. 2006-20755 discloses a technique for a portable medical apparatus which circulates air in the apparatus using an exhaust fan to cool the apparatus without the need for forced exhaust from the apparatus.

On the other hand, Japanese Patent Application Laid-Open Publication No. 2006-202869 discloses a technique for a box-shaped apparatus which eliminates the need for an exhaust fan by distributing louvers along the width of an exhaust passage of cooling air from multiple blowers with the longitudinal direction of each louver turned a predetermined angle to control exhaust directions of the cooling air.

SUMMARY OF THE INVENTION

The present invention provides an interior cooling structure including: a frame in which a plurality of circuit board modules are stacked, with electronic components mounted on the plurality of circuit board modules by being classified by function; an external housing which covers the frame together with the plurality of circuit board modules; a plurality of cooling devices which reduce temperature rises in the external housing caused by heat produced by the plurality of circuit board modules; and a heat generating region partitioned in such away as to enclose a circuit board module which has the highest total power consumption out of the plurality of circuit board modules, wherein the plurality of cooling devices are arranged in such away as to reduce temperature rises in the heat generating region by displaying capacity higher than capacity of each of the cooling devices.

Also, the present invention provides an ultrasound imaging apparatus equipped with an interior cooling structure which includes: a frame in which a plurality of circuit board modules are stacked, with electronic components mounted on the plurality of circuit board modules by being classified by function; an external housing which covers the frame together with the plurality of circuit board modules; a plurality of cooling devices which reduce temperature rises in the external housing caused by heat produced by the plurality of circuit board modules; and a heat generating region partitioned in such away as to enclose a circuit board module which has the highest total power consumption out of the plurality of circuit board modules, wherein the plurality of cooling devices are arranged in such away as to reduce temperature rises in the heat generating region by displaying capacity higher than capacity of each of the cooling devices.

The above and other objects, features and advantages of the invention will become more clearly understood from the following description referring to the accompanying drawings.

DETAILED DESCRIPTION OF THE PREFERRED EMBODIMENTS

An embodiment of the present invention will be described below with reference to the drawings. The present embodiment will be described taking as an example an interior cooling structure for electronic circuit boards installed in an ultrasound endoscope apparatus which is an ultrasound medical apparatus, and more particularly, an ultrasound imaging apparatus.

Figure 1:
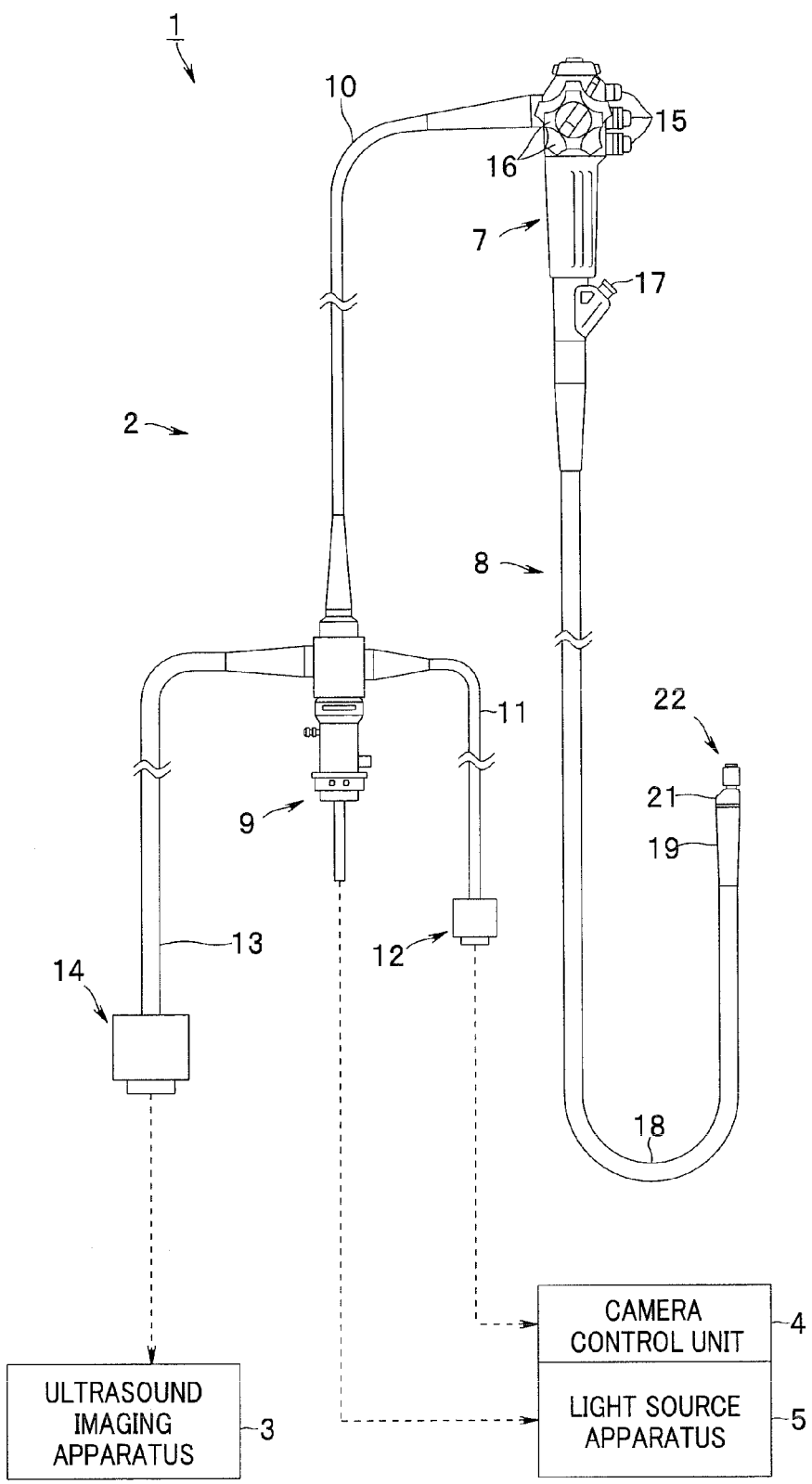
FIG. 1 is a diagram illustrating a schematic configuration of an ultrasound endoscope according to one embodiment of the present invention.
Figure 2:
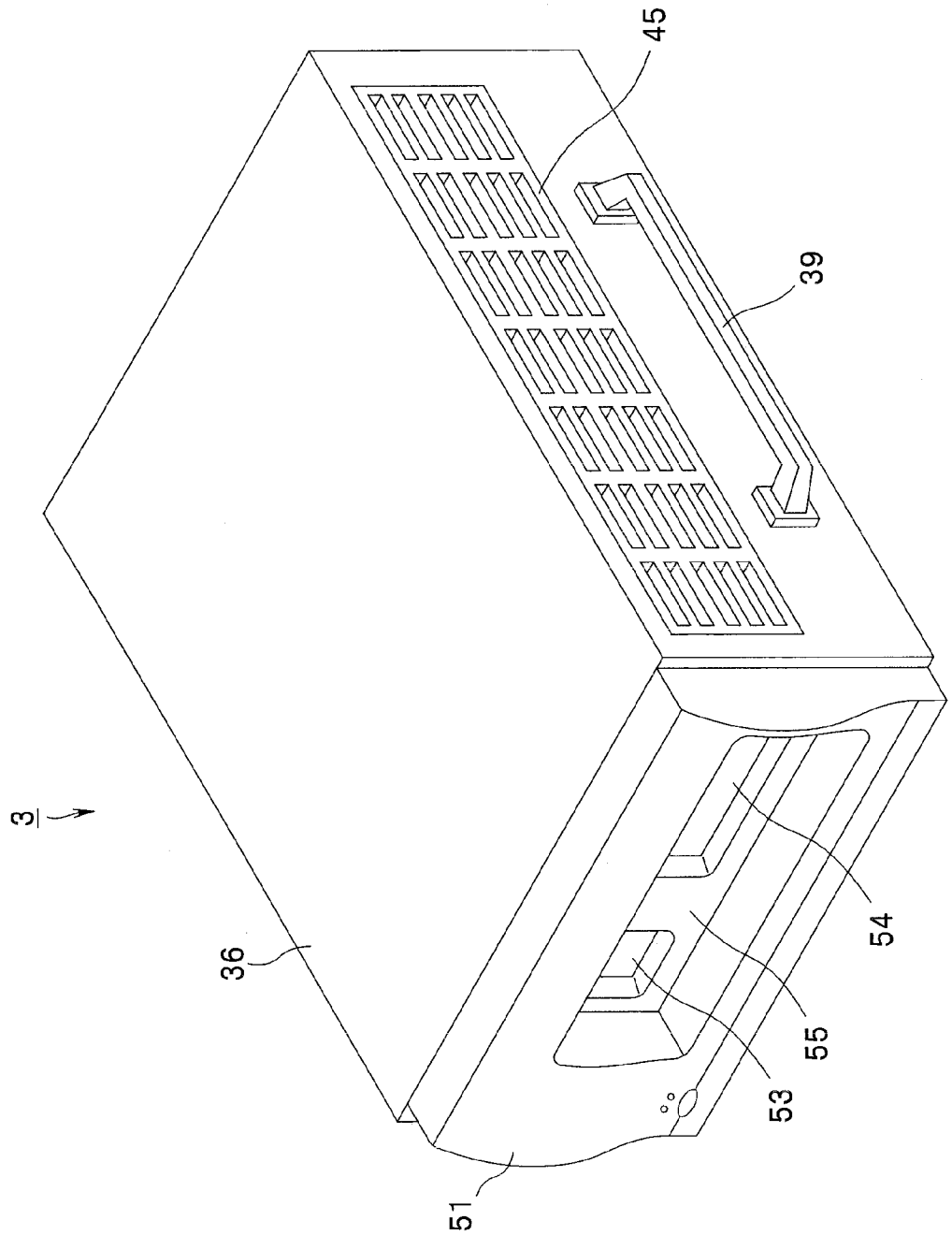
FIG. 2 is a perspective view showing an overall configuration of the ultrasound imaging apparatus according to the embodiment of the present invention.
Figure 3:
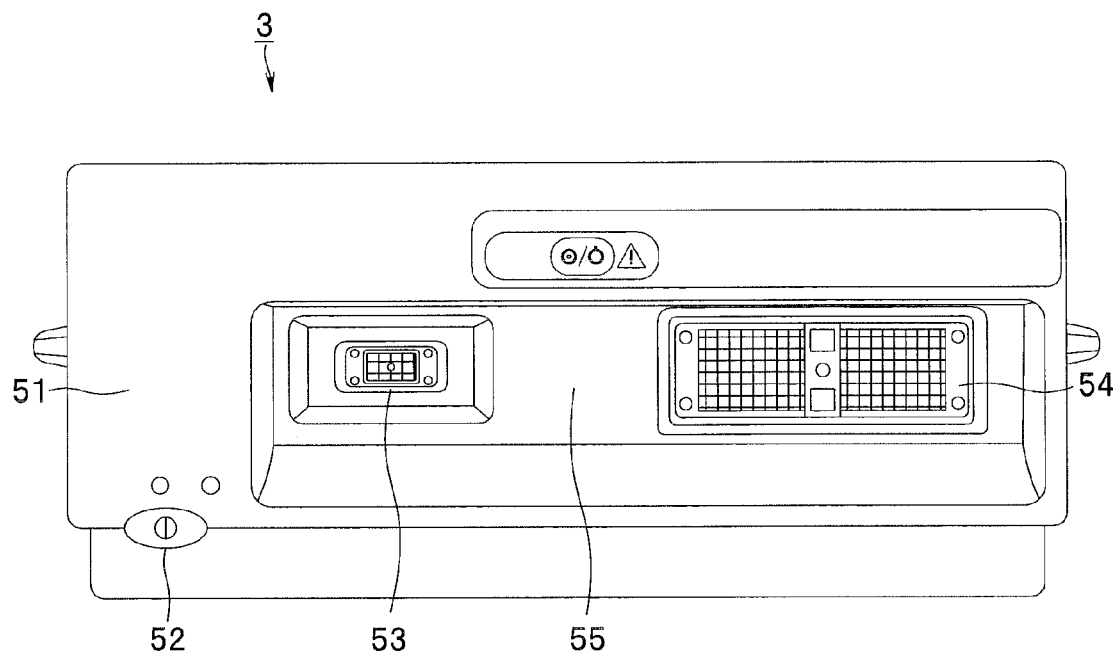
FIG. 3 is a plan view of the ultrasound imaging apparatus according to the embodiment of the present invention.
Figure 4:
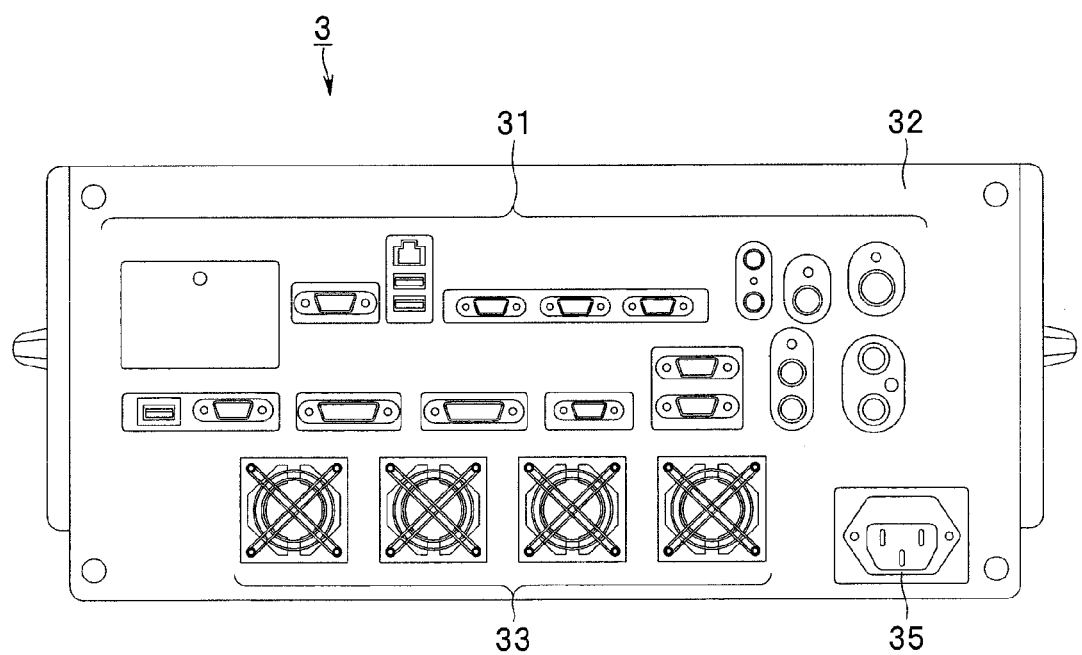
FIG. 4 is a back view of the ultrasound imaging apparatus according to the embodiment of the present invention.
Figure 5:
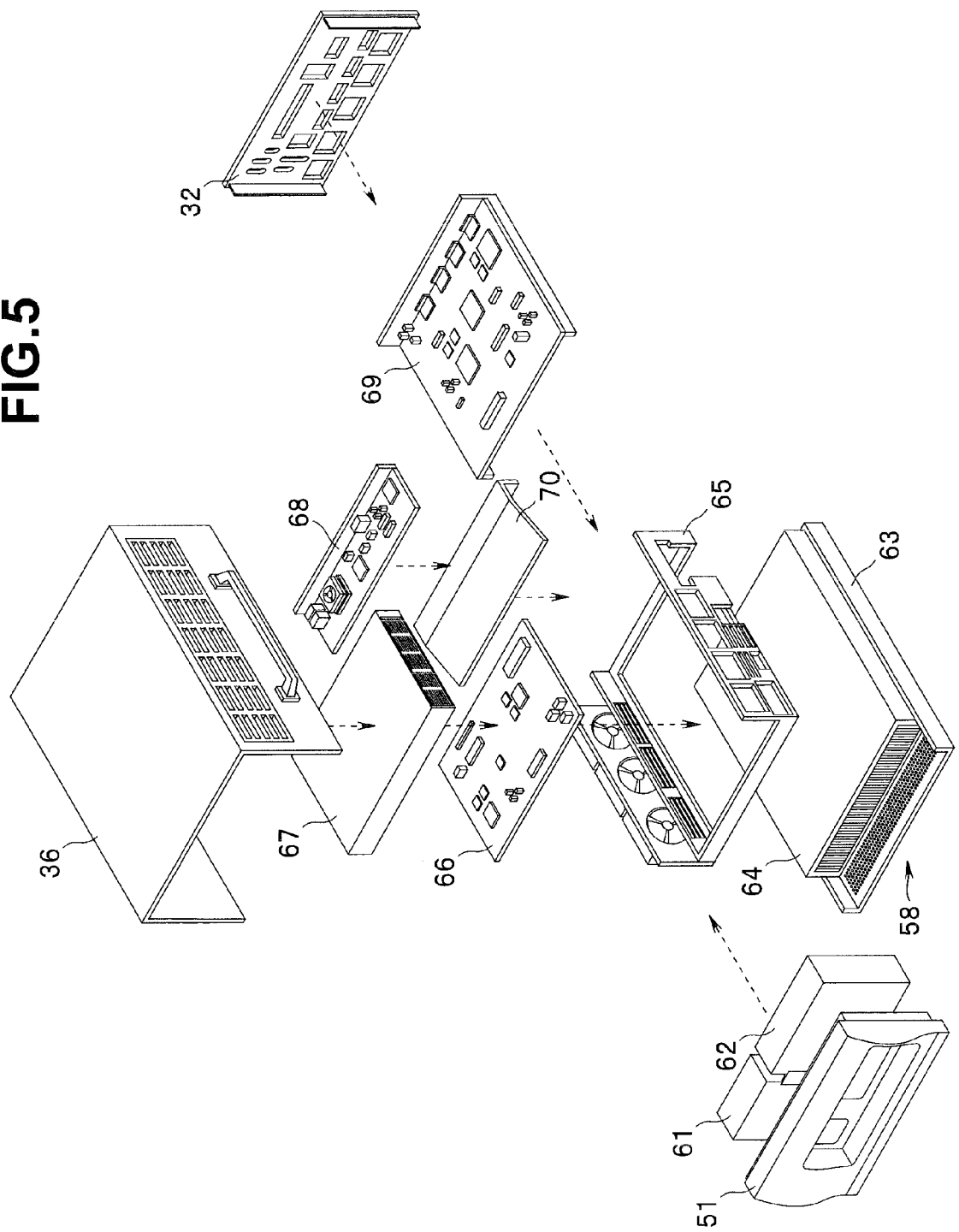
FIG. 5 is an exploded perspective view of the ultrasound imaging apparatus according to the embodiment of the present invention.
Figure 6:
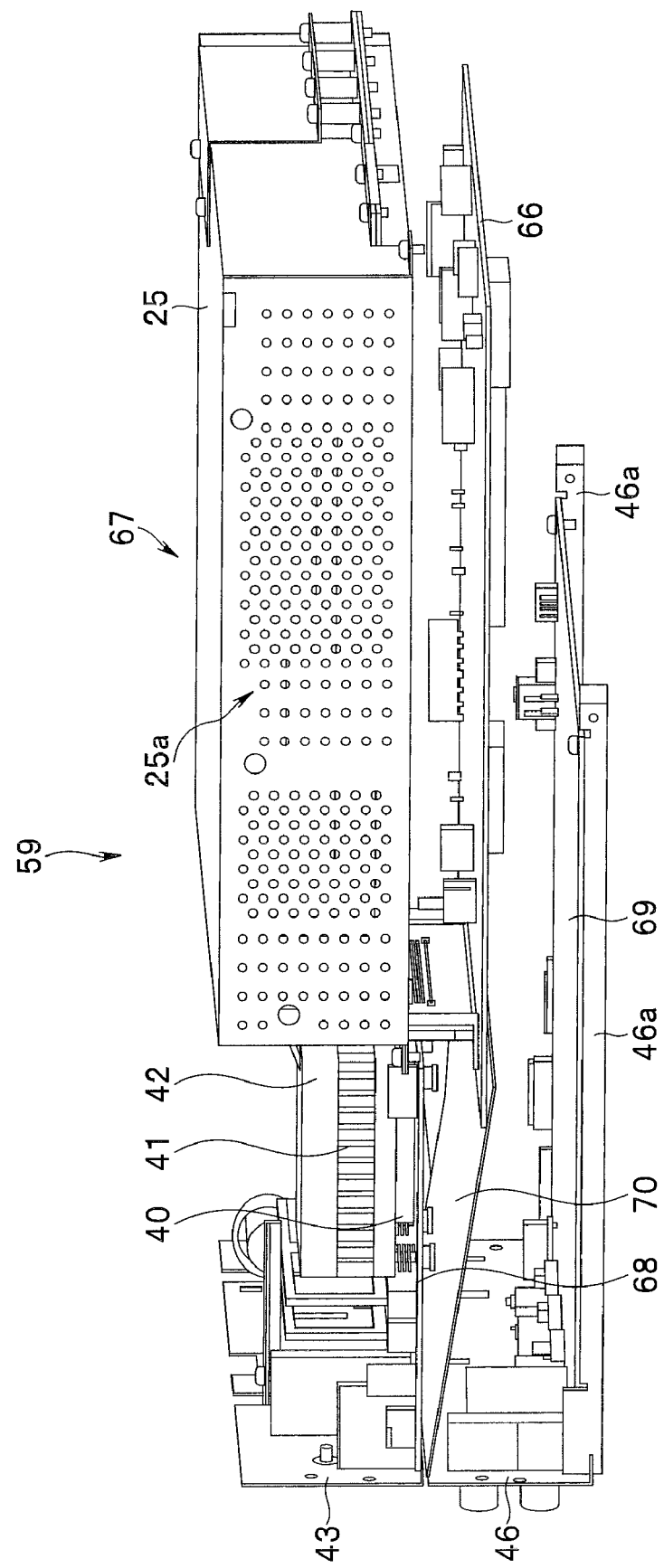
FIG. 6 is a perspective view showing a configuration of a printed circuit board unit in the ultrasound imaging apparatus according to the embodiment of the present invention.
Figure 7:
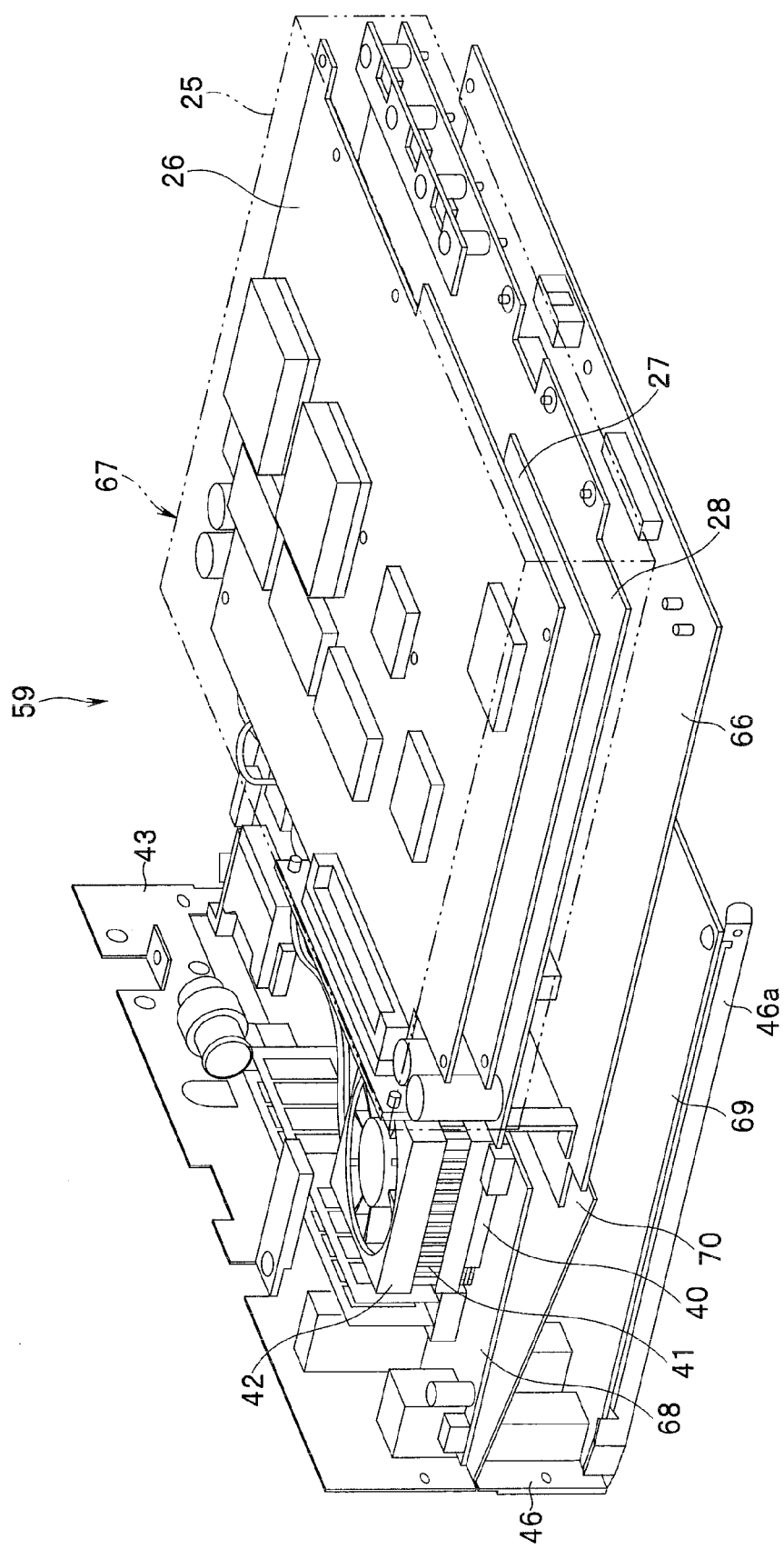
FIG. 7 is a perspective view showing the configuration of the printed circuit board unit in the ultrasound imaging apparatus according to the embodiment of the present invention, as viewed from a different angle.
Figure 8:
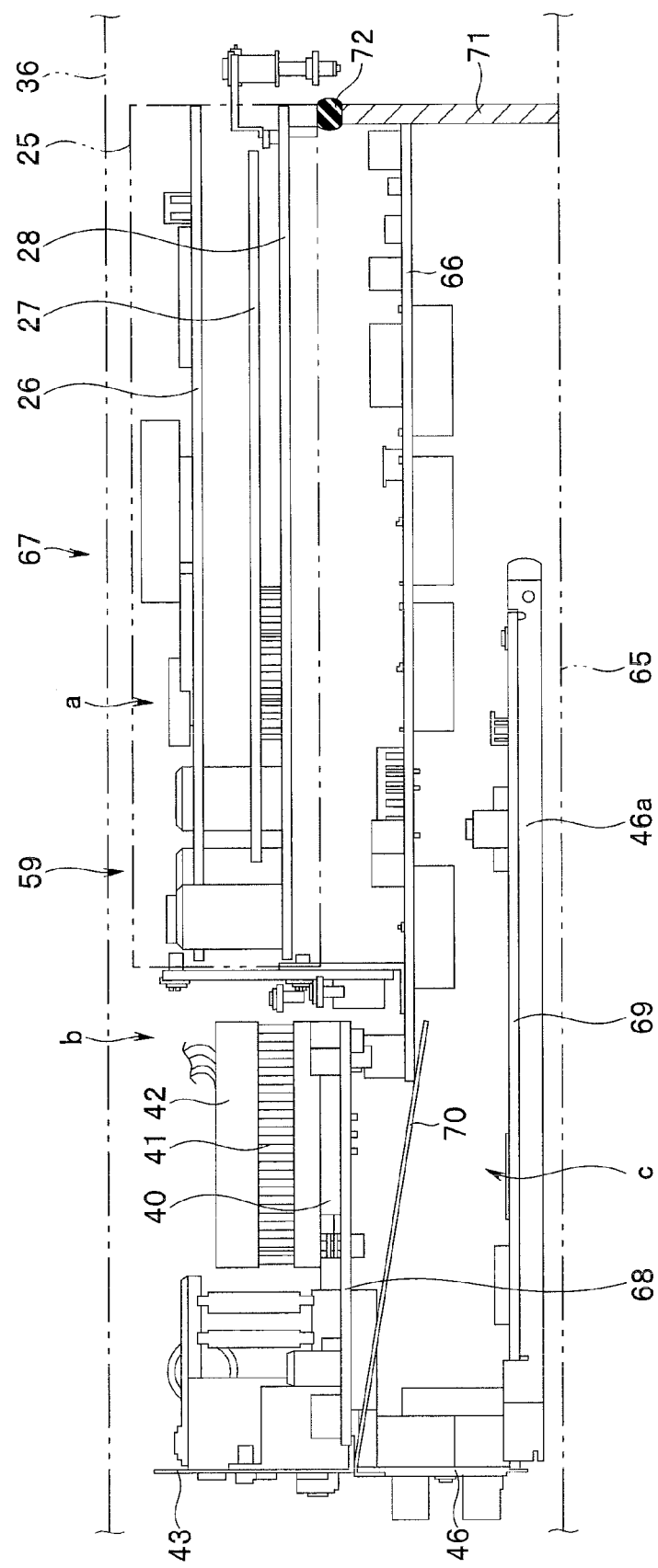
FIG. 8 is a side view showing the configuration of the printed circuit board unit according to the embodiment of the present invention.
Figure 9:
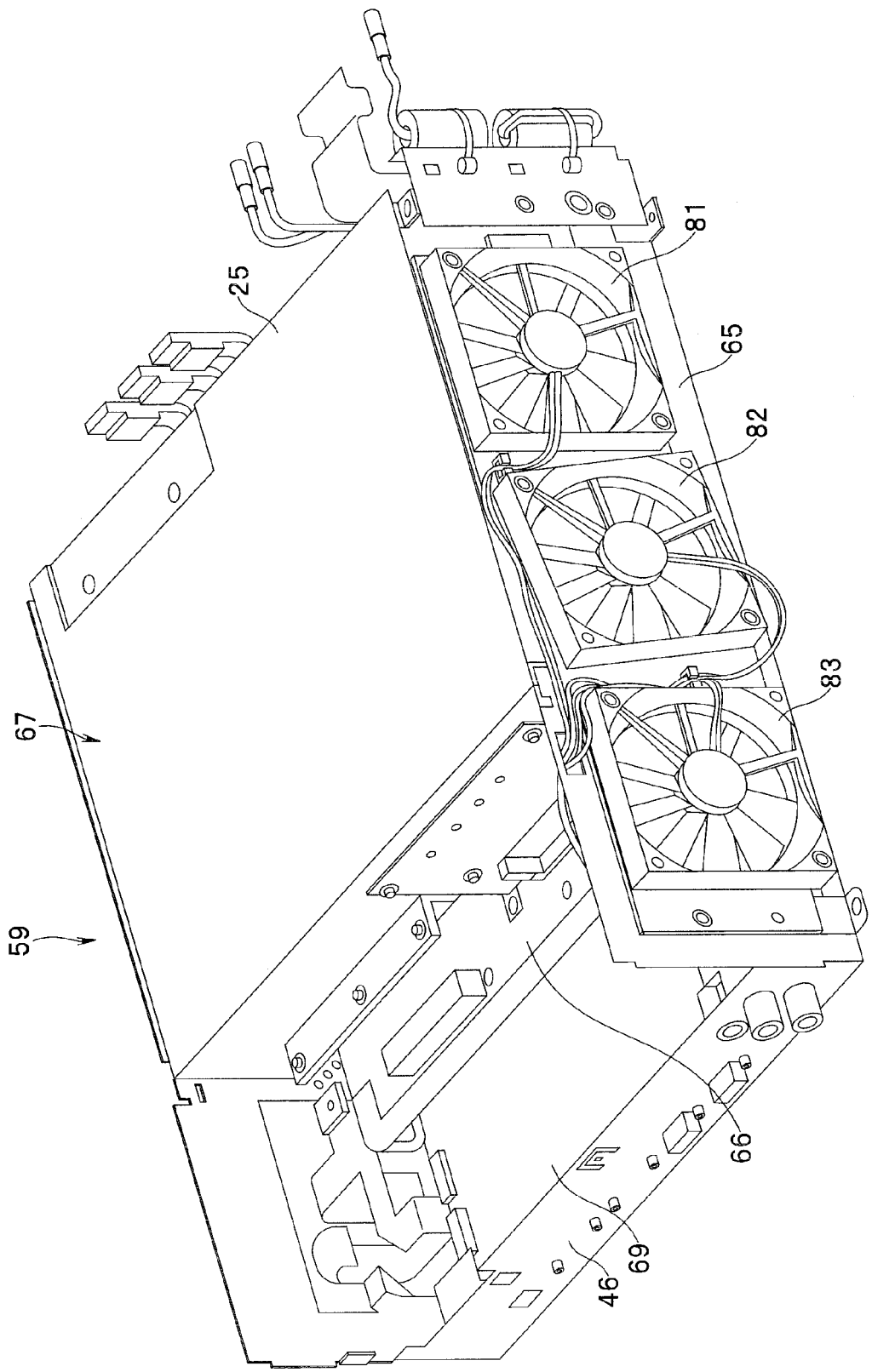
FIG. 9 is a perspective view illustrating an assembly process of the printed circuit board unit according to the embodiment of the present invention.
Figure 10:
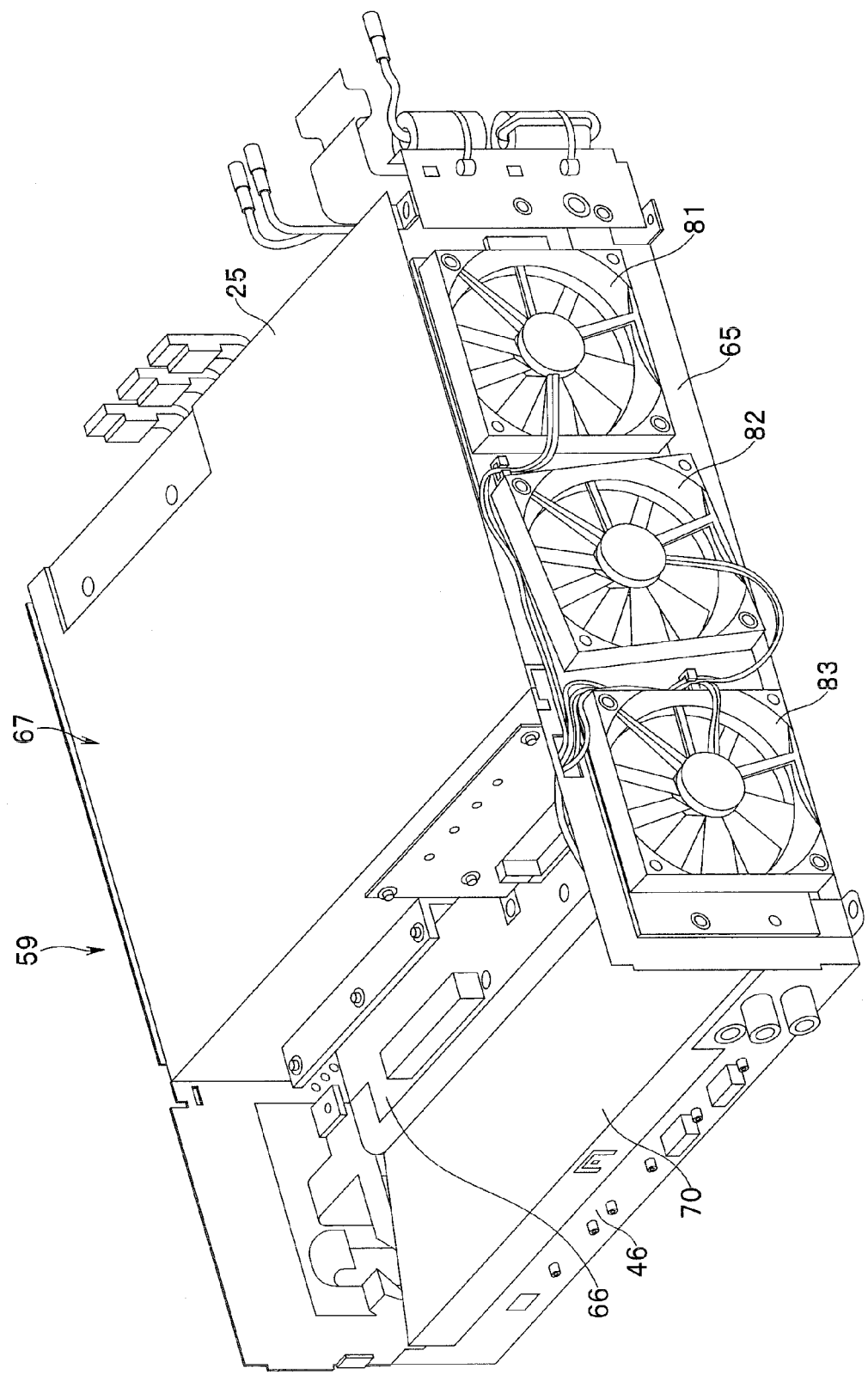
FIG. 10 is a perspective view illustrating the printed circuit board unit after a shielding member is mounted in a state shown in FIG. 9, according to the embodiment of the present invention.
Figure 11:
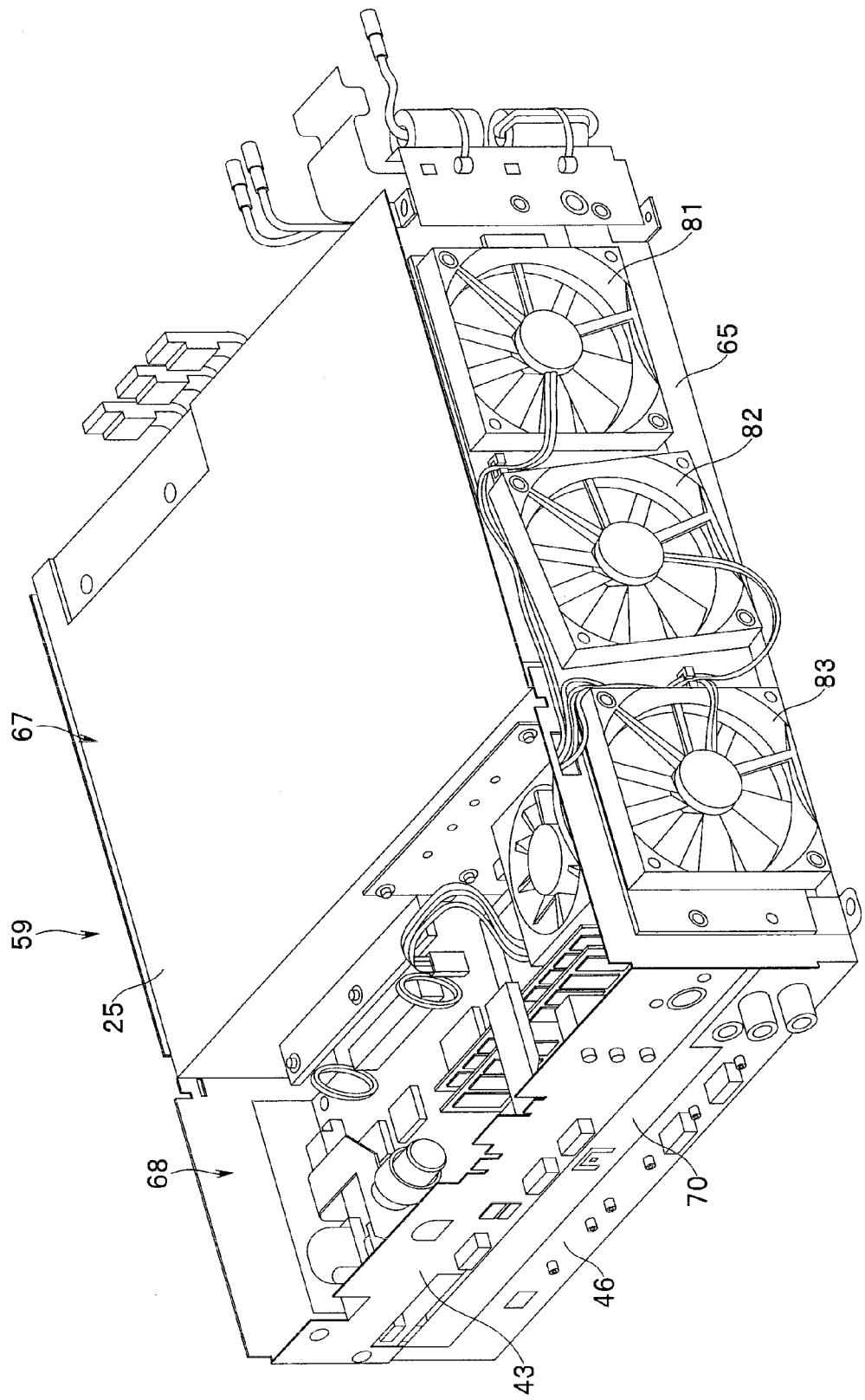
FIG. 11 is a perspective view illustrating the printed circuit board unit after a control board is mounted in a state shown in FIG. 10, according to the embodiment of the present invention.
Figure 12:
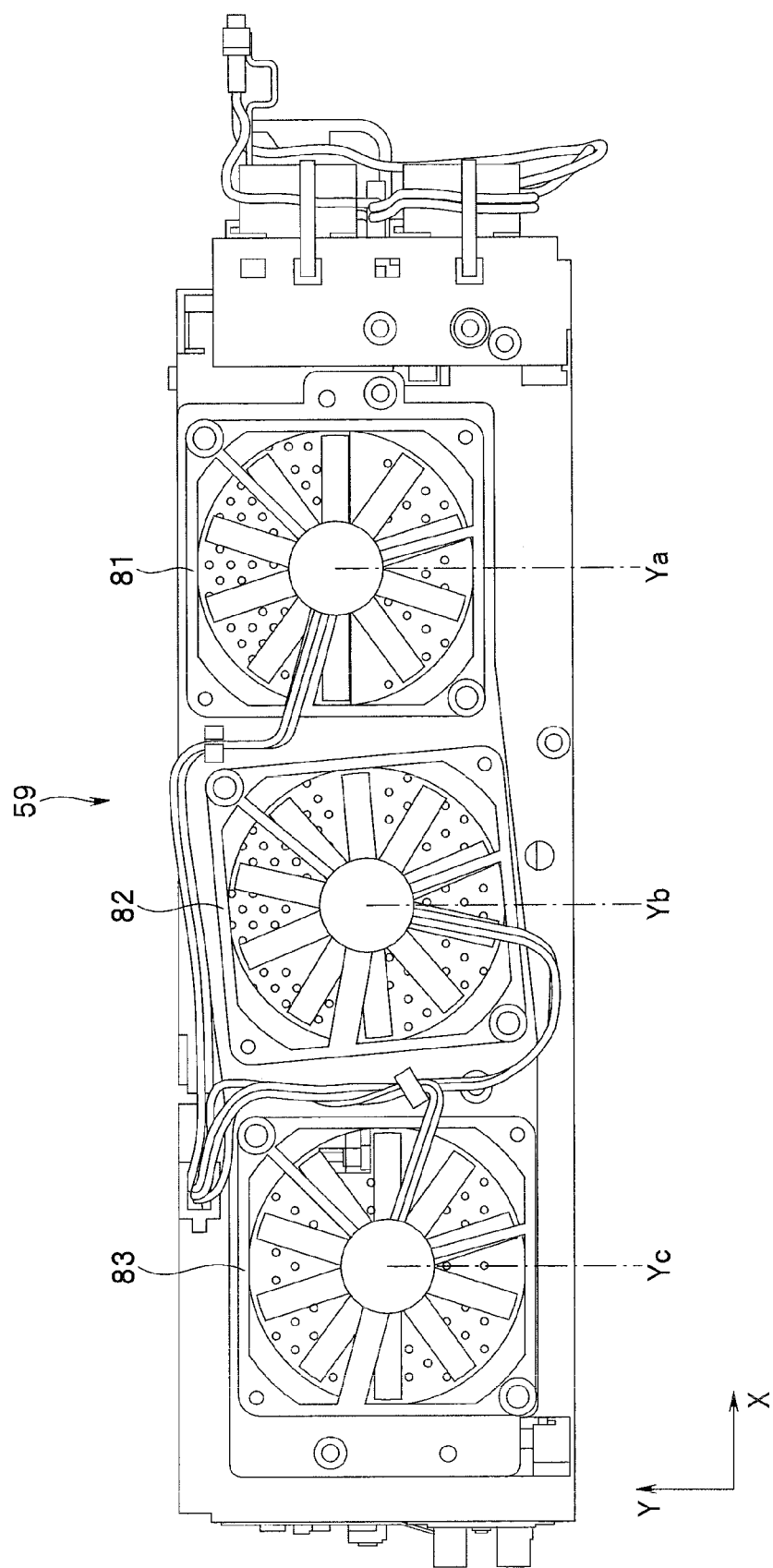
FIG. 12 is a side view of the printed circuit board unit with fans mounted to reduce temperature rises in the printed circuit board unit, according to the embodiment of the present invention.
Figure 13:
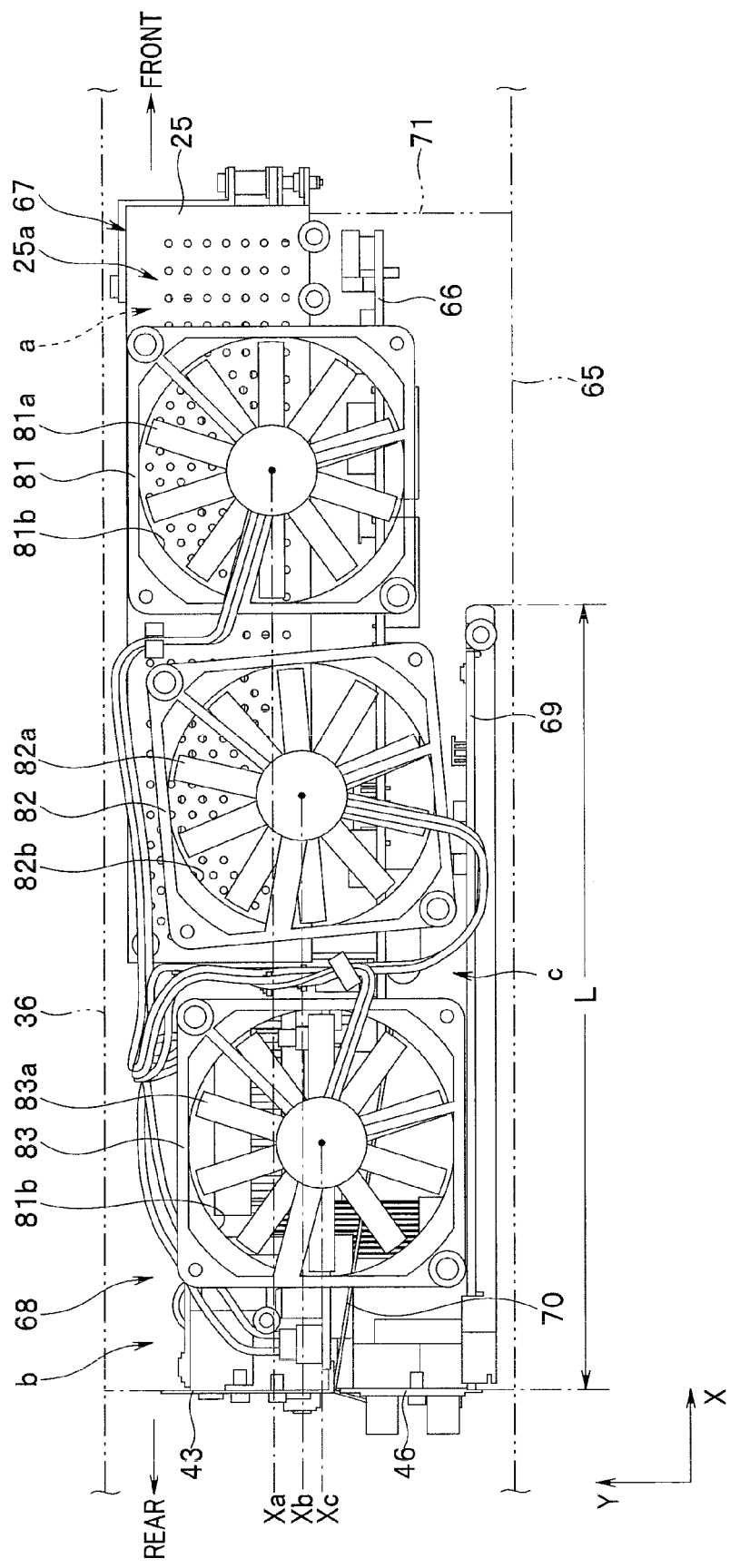
FIG. 13 is a plan view illustrating a layout configuration of the fans shown in FIG. 12, according to the embodiment of the present invention.

FIGS. 1 to 13 shows the embodiment of the present invention, where FIG. 1 is a diagram illustrating a schematic configuration of an ultrasound endoscope; FIG. 2 is a perspective view showing an overall configuration of the ultrasound imaging apparatus; FIG. 3 is a plan view of the ultrasound imaging apparatus; FIG. 4 is a back view of the ultrasound imaging apparatus; FIG. 5 is an exploded perspective view of the ultrasound imaging apparatus; FIG. 6 is a perspective view showing a configuration of a printed circuit board unit in the ultrasound imaging apparatus; FIG. 7 is a perspective view showing the configuration of the printed circuit board unit in the ultrasound imaging apparatus, as viewed from a different angle; FIG. 8 is a side view showing the configuration of the printed circuit board unit; FIG. 9 is a perspective view illustrating an assembly process of the printed circuit board unit; FIG. 10 is a perspective view illustrating the printed circuit board unit after a shielding member is mounted in a state shown in FIG. 9; FIG. 11 is a perspective view illustrating the printed circuit board unit after a control board is mounted in a state shown in FIG. 10; FIG. 12 is a side view of the printed circuit board unit with cooling devices mounted to reduce temperature rises in the printed circuit board unit; and FIG. 13 is a plan view illustrating a layout configuration of the cooling devices shown in FIG. 12.

As shown in FIG. 1 an ultrasound endoscope apparatus 1 which is an ultrasound medical apparatus according to the present embodiment mainly includes an ultrasound endoscope 2, ultrasound imaging apparatus 3, camera control unit (hereinafter abbreviated to CCU) 4, and light source apparatus 5. The ultrasound imaging apparatus 3 and CCU 4 are connected with a monitor (not shown) to display ultrasound images and endoscopic images produced by the ultrasound endoscope 2.

The ultrasound endoscope 2 mainly includes an elongated insertion portion 8 inserted into a body cavity, operation portion 7 located at a proximal end portion of the insertion portion 8, and universal cord 10 which extends from a flank of the operation portion 7.

An endoscope connector 9 connected with the light source apparatus 5 is provided at a proximal end portion of the universal cord 10. Extending from the endoscope connector 9, an electrical cable 11 is detachably connected to the CCU 4 via an electrical connector 12 and an ultrasound cable 13 is detachably connected to the ultrasound imaging apparatus 3 via an ultrasound connector 14.

Starting from a distal side, the insertion portion 8 of the ultrasound endoscope 2 includes a distal rigid portion 21 made of rigid resin, a bendable, bending portion 19 located at a rear end of the distal rigid portion 21, and a small-diameter, elongated, flexible tubular portion 18 located at a rear end of the bending portion 19 and extending to a distal end portion of the operation portion 7, all of which are installed in a connected row arrangement. Besides, an ultrasound transducer portion 22 which includes an array of multiple electronic-scanning ultrasound transducers used to send and receive ultrasound is provided on a distal side of the distal rigid portion 21.

Also, the operation portion 7 of the ultrasound endoscope 2 has an angle knob 16 used to control bending of the bending portion 19 in a desired direction; various buttons 15 for air/water supply, suction, and other operations; and a treatment instrument insertion port 17 which provides an entrance for treatment instruments introduced into a body cavity.

A distal end face of the distal rigid portion 21 where the ultrasound transducer portion 22 is provided is also arranged with an illumination lens cover of an illumination optical system, an observation lens cover of an observation optical system, and a forceps port which doubles as a suction port, and air/water supply nozzle (not shown). The distal rigid portion 21 contains image pickup means (not shown) which is an image sensor such as a CCD or CMOS to collect and photoelectrically convert photographic light introduced through the observation lens cover.

Incidentally, although the electronic-scanning ultrasound endoscope 2 connected to the ultrasound imaging apparatus 3 has been illustrated in FIG. 1, this is not restrictive and the ultrasound imaging apparatus 3 according to the present embodiment can also be connected with a mechanical-scanning ultrasound endoscope.

Next, a configuration of the ultrasound imaging apparatus 3 connected with the ultrasound endoscope 2 will be described below with reference to FIGS. 2 to 4.

As shown in FIGS. 2 and 3, the ultrasound imaging apparatus 3 includes a power switch 52 disposed on a front panel 51 and two different types of apparatus-side ultrasound connector 53 and 54 installed side by side on an apparatus-side connector mounting surface 55 formed on the front panel 51.

On the left side of the apparatus-side connector mounting surface 55 as viewed in FIG. 2 or 3, there is a first apparatus-side ultrasound connector 53 according to the present embodiment which is, for example, a 96-wire plug connector paired with an ultrasound connector of a mechanical-scanning ultrasound medical apparatus.

On the right side of the apparatus-side connector mounting surface 55 as viewed in FIG. 2 or 3, there is a second apparatus-side ultrasound connector 54 according to the present embodiment which is, for example, a 260-wire plug connector paired with an ultrasound connector of an electronic-scanning ultrasound medical apparatus.

As shown in FIG. 4, on a rear panel 32 of the ultrasound imaging apparatus 3, there are connection terminals 31 connected with multiple communications cables, a power connector 35 connected with a power cable, and multiple (four according to the present embodiment) cooling fans 33. The four cooling fans 33 function as exhaust fans to reduce temperature rises in a power supply unit 64 (described later).

The connection terminals 31 are disposed on an upper side of the rear panel 32 serving as a backplane. The power connector 35 is disposed at the lower right of the rear panel 32.

Furthermore, as shown in FIG. 2, the ultrasound imaging apparatus 3 has a cover unit 36 which forms opposite flanks and a top face of the housing's exterior. On a flank of the cover unit 36, there are vent holes 45 serving as intake ports and a handle 39 for a user to grip during carriage.

Next, an internal configuration of the ultrasound imaging apparatus 3 will be described below with reference to FIG. 5.

As shown in FIG. 5, the ultrasound imaging apparatus 3 mainly includes the front panel 51 (described above) which forms a front face of an external housing; two interface units 61 and 62 provided at the back face of the front panel 51; the power supply unit 64 fixedly placed on a plate-like base frame 63 which forms a bottom face of the external housing; a board frame 65 which provides an electronic-board support, a fan unit being provided on a flank of the electronic-board support to serve as cooling devices; a signal processing board 66; a digital beam forming unit (DBF unit) 67; a control board 68 on which a CPU is mounted; a video processing board 69; a partition plate 70 which doubles as an electromagnetic shield and partitions the interior of the apparatus; the rear panel 32 (described above) which forms a back face of the external housing; and the cover unit 36 (described above) which forms the opposite flanks and top face of the external housing. The two interface units 61 and 62—one of which is a mechanical-scanning interface unit 61 and the other of which is an electronic-scanning interface unit 62—are fixedly coupled with each other.

That is, the ultrasound imaging apparatus 3 is configured such that the front panel 51, base frame 63, rear panel 32, and cover unit 36 form the external housing which, being approximately box-shaped, contains the interface units 61 and 62, power supply unit 64, board frame 65, signal processing board 66, DBF unit 67, control board 68, partition plate 70, and video processing board 69.

Next, the power supply unit 64 and board layout in the ultrasound imaging apparatus 3 will be described.

First, in the ultrasound imaging apparatus 3, the power supply unit 64 is screw-fastened to the lowermost part of the base frame 63. Then, two interface units 61 and 62 are screw-fastened to that part of the base frame 63 which is located in front of the power supply unit 64 by accessing from the front. The board frame 65 is screw-fastened onto the power supply unit 64. The base frame 63 with the power supply unit 64 mounted makes up a base unit 58.

Firstly, the signal processing board 66 is screw-fastened to the board frame 65 by accessing vertically downward. Screw holes (not shown) are provided in the board frame 65 such that the signal processing board 66 will be spaced a predetermined distance away from the power supply unit 64. That is, the signal processing board 66 is fastened to the board frame 65 by being raised halfway in a vertical direction.

The DBF unit 67 is screw-fastened to the uppermost position of the board frame 65 by accessing upper front part of the board frame 65 vertically downward. That is, the DBF unit 67 is installed above the signal processing board 66. This is intended to ease electrical interconnection by placing the DBF unit 67 and signal processing board 66 close to each other.

The control board 68 is screw-fastened to upper rear part of the board frame 65. At this time, the partition plate 70 is screw-fastened to lower part of a rear edge of the signal processing board 66 while sandwiched between a terminal plate (described later) provided on a rear edge of the signal processing board 66 and terminal plate (described later) provided on a rear edge of the video processing board 69. The partition plate 70 is thereby fixed, hanging in such a way as to cover a rear opening behind the signal processing board 66.

The video processing board 69 is slid forward to between the power supply unit 64 and signal processing board 66 in a horizontal direction from the rear side of the board frame 65 and fastened to the board frame 65 with screws. The video processing board 69 has been fastened to a sliding board base, and when the board base is screw-fastened to the board frame 65, the video processing board 69 is fastened to the board frame 65 together with the board base.

As described above, the circuit board modules—the signal processing board 66, DBF unit 67, control board 68, and video processing board 69—are fastened in a stacked state to the board frame 65 installed on the base unit 58 (see FIGS. 6 to 8). According to the present embodiment, the signal processing board 66, DBF unit 67, control board 68, and video processing board 69 stacked on the base unit 58 makes up a printed circuit board unit (PCB unit) 59 (see FIG. 11).

The boards 66, 68, and 69 and units 61, 62, and 67 of the PCB unit 59 are electrically connected to a common board (not shown), thereby establishing an electrical circuit configuration. According to the present embodiment, plug-type board-to-board connectors (not shown) are used for the electrical connection. A harness may be used for board-to-board electrical connections, but the use of plug-type board-to-board connectors, of course, can complete board-to-board electrical connections simultaneously with installation and fastening of the boards.

Furthermore, the PCB unit 59 is electrically connected with the power supply unit 64 of the base unit 58 via a harness (not shown) to draw power from the power supply unit 64 via the harness. Incidentally, the PCB unit 59 according to the present embodiment is a unit formed by assembling the boards 66, 68, and 69, on which electronic components are mounted, and the DBF unit 67. Thus, the entire PCB unit 59 can be replaced by being removed from the base unit 58.

As described above, the ultrasound imaging apparatus 3 according to the present embodiment makes it possible to downsize the PCB unit 59 by stacking the multiple circuit boards in the PCB unit 59 and thereby downsize the entire apparatus compared to conventional apparatus.

Next, configuration of the signal processing board 66, DBF unit 67, control board 68, and video processing board 69 contained in the downsized PCB unit 59 will be described with reference to FIGS. 6 to 11.

As shown in FIGS. 6 to 8, the DBF unit 67 mainly includes a box-shaped casing 25 made of electromagnetic shielding material to prevent electromagnetic interference and three electronic circuit boards 26, 27, and 28 fixedly placed in the casing 25, where multiple vent holes 25a are formed in opposite flanks of the casing 25.

Electronic components such as an analog/digital (AD) converter, digital signal processor (DSP), and field programmable gate array (FPGA) are mounted on the electronic circuit board 26 fixedly placed in the uppermost part of the casing 25 out of the three electronic circuit boards 26, 27, and 28. Electronic components such as field effect transistors (FETs), other transistors, and diodes are mounted on the electronic circuit board 27 fixedly placed in middle part of the casing 25.

Electronic components such as amplifiers and capacitors are mounted on the electronic circuit board 28 fixedly placed in the lowermost part of the casing 25.

In this way, the DBF unit 67 is configured such that the three electronic circuit boards 26, 27, and 28 stacked in three layers are covered by the casing 25. Total power consumption of the three electronic circuit boards 26, 27, and 28 is, for example, 130 W according to the present embodiment, with the uppermost electronic circuit board 26 consuming the most power and the lowermost electronic circuit board 28 consuming the least power.

That is, of the total power consumption of 130 W by the DBF unit 67, the power consumption by the electronic components such as the AD converter, DSP, and FPGA mounted on the electronic circuit board 26 is the highest, the power consumption by the electronic components such as the FETs, other transistors, and diodes mounted on the electronic circuit board 27 is the next highest, and the power consumption by the electronic components such as the amplifiers and capacitors mounted on the electronic circuit board 28 is the lowest.

In this way, the DBF unit 67 is configured such that the electronic circuit boards are placed from top to bottom in order of decreasing power consumption, with the electronic circuit board 26 which consumes the most power being placed in the uppermost part because of the largest amount of heat generation and the electronic circuit board 28 which consumes the least power being placed in the lowermost part because of the smallest amount of heat generation.

Components mounted on the control board 68 includes a central processing unit (CPU) 40, a heat sink 41 placed on the CPU 40, a CPU fan 42 which cools the heat sink 41 by sending air, and a memory. Power consumption of the control board 68 is, for example, 43 W according to the present embodiment. Incidentally, a terminal plate 43 is attached to the control board 68 in such a way as to be perpendicular to the control board 68, with part of the connection terminals 31 being disposed behind the terminal plate 43.

The signal processing board 66 and video processing board 69 consume, for example, 13 W each according to the present embodiment. Incidentally, a terminal plate 46 is attached to the video processing board 69 in such a way as to be perpendicular to the video processing board 69, with part of the connection terminals 31 being disposed behind the terminal plate 46. The video processing board 69 is formed integrally with the terminal plate 46 in such a way as to be able to slide forward in the horizontal direction from the rear side of the board frame 65 and is fixedly placed on a sliding base 46a which extends downward to opposite edges of the video processing board 69.

Thus, the PCB unit 59 is configured such that circuit boards are placed as follows: the DBF unit 67 which consumes the most power is placed in the uppermost part, the control board 68 which consumes the second most power is placed at the rear slightly below the DBF unit 67, and the signal processing board 66 which consumes the least power and the video processing board 69 are placed below the DBF unit 67.

Incidentally, since the signal processing board 66 and video processing board 69 consume the same amount of power, the locations of the two circuit boards may of course be exchanged. If the two circuit boards differ in power consumption, the one with higher power consumption may be placed above the other.

With the above configuration, after the base unit 58 and PCB unit 59 are connected electrically, the front panel 51, cover unit 36, and rear panel 32 are fastened with screws, thereby completing assembly of the ultrasound imaging apparatus 3 according to the present embodiment shown in FIG. 2.

When the ultrasound imaging apparatus 3 thus configured is ready for operation, a sectional space partitioned into three heat generating regions a, b, and c in a longitudinal direction is formed in the PCB unit 59.

Specifically, as shown in FIGS. 8 to 11, a region surrounded by the casing 25 of the DBF unit 67 is designated as a first heat generating region a, where the casing 25 is made of electromagnetic shielding material. That is, the first heat generating region a is the partitioned region which develops the largest amount of heat in the ultrasound imaging apparatus 3 with the electronic components in the DBF unit 67 which consumes the most power during operation of the ultrasound imaging apparatus 3 acting as heat sources.

Next, as shown in FIGS. 8 and 11, a second heat generating region b is the region which is surrounded by the DBF unit 67 and cover unit 36 on the top side, the signal processing board 66 and partition plate 70 on the bottom side, the terminal plate 43 of the control board 68 on the rear side, and a plate 71 on the front side, the plate 71 extending vertically upward from the board frame 65, where the partition plate 70 and the plate 71 are made of electromagnetic shielding material. That is, the second heat generating region b is the partitioned region which develops the second largest amount of heat in the ultrasound imaging apparatus 3 with the electronic components in the control board 68 which consumes the second most power and the electronic components in the signal processing board 66 which consumes the least power during operation of the ultrasound imaging apparatus 3 acting together as heat sources.

Furthermore, as shown in FIGS. 8 and 10, a third heat generating region c is the region which is surrounded by the signal processing board 66 and partition plate 70 on the top side, the board frame 65 on the bottom side, the terminal plate 46 of the video processing board 69 on the rear side, and the plate 71 on the front side. That is, the third heat generating region c is the partitioned region which develops the third largest amount of heat in the ultrasound imaging apparatus 3 with the electronic components in the video processing board 69 which consumes the least power during operation of the ultrasound imaging apparatus 3 acting as heat sources.

Incidentally, as shown in FIG. 8, a gasket 72 is provided over an entire upper end face of the plate 71 fastened to the board frame 65 to prevent the plate 71 from creating a gap as well as to keep the plate 71 in contact with a bottom face of the DBF unit 67. The gasket 72 doubles as an electromagnetic shield to prevent the ultrasound imaging apparatus 3 from obstructing operation of external apparatus by electromagnetic interference, and thereby ensure electromagnetic compatibility (EMC).

Also, the partition plate 70, which is made of electromagnetic shielding material, can prevent electromagnetic interference between the video processing board 69 and the control board 68 provided above the video processing board 69, in particular. In this way, the partition plate 70 doubles as a shield to reduce electromagnetic noise in each circuit configuration.

As described above, in the PCB unit 59 of the ultrasound imaging apparatus 3 according to the present embodiment, the interior of the external housing formed by the front panel 51, base frame 63, rear panel 32, and cover unit 36 is partitioned into the three heat generating regions a, b, and c. Also, as shown in FIGS. 12 and 13, three fans (blowers) 81, 82, and 83 are installed side by side on a flank of the board frame 65. The three fans 81, 82, and 83, which function as cooling devices with equal ventilation capacity, exhaust heated air from the three heat generating regions a, b, and c and thereby keep air in the heat generating regions a, b, and c below the maximum ambient operating temperature of the electronic components.

The three fans 81, 82, and 83 are arranged on a flank of the board frame 65 in such a way that centers (centers of rotation of multiple blades) of the three fans 81, 82, and 83 will be located, respectively, on three axes Y$a$, Y$b$, and Y$c$ spaced a predetermined distance away from each other along a longitudinal direction of the PCB unit 59 (in an X-axis direction in FIGS. 12 and 13).

Also, in the PCB unit 59 according to the present embodiment, the DBF unit 67, control board 68, signal processing board 66, and video processing board 69 are stacked such that the total amounts of power consumption of electronic components will decrease with vertical descent (along a Y-axis in FIGS. 12 and 13). At the same time, the PCB unit 59 is partitioned into the three heat generating regions a, b, and c such that the amounts of developed heat will decrease in the order a, b, and c.

Thus, as shown in FIG. 13, a first fan 81, second fan 82, and third fan 83 are arranged from the front side to the rear side with their center (center of rotation of multiple blades) positions shifted stepwise vertically downward (along the Y-axis in FIG. 13) to efficiently reduce temperature rises in the three heat generating regions a, b, and c. Specifically, the center (center of rotation of multiple blades 81a) of the first fan 81 is located on an Xa axis, center (center of rotation of multiple blades 82a) of the second fan 82 is located on an Xb axis vertically lower than the Xa axis along the Y-axis, and center (center of rotation of multiple blades 83a) of the third fan 83 is located on an Xc axis vertically lower than the Xb axis along the Y-axis.

More specifically, the first fan 81 provided on the frontmost side is intended to exhaust air from the first heat generating region a which causes the highest temperature rise and second heat generating region b which causes the second highest temperature rise. The first fan 81, whose multiple blades 81a exhaust air through an opening 81b, is placed such that approximately 60% the surface area of the opening 81b will cover the first heat generating region a and that the remaining approximately 40% the surface area of the opening 81b will cover the second heat generating region b.

The second fan 82 provided in the center is intended to exhaust air from the first heat generating region a, the second heat generating region b, and the third heat generating region c which causes the lowest temperature rise. The second fan 82, whose multiple blades 82a exhaust air through an opening 82b, is placed such that approximately 47% the surface area of the opening 82b will cover the first heat generating region a and that the remaining approximately 53% the surface area of the opening 82b will cover the second heat generating region b and third heat generating region c.

Since the three fans 81, 82, and 83 are arranged side by side in a limited placement area on a flank of the board frame 65, the second fan 82 is placed at a slight angle around the multiple blades 82a to the other two fans 82 and 83. Incidentally, to fit in length L of the video processing board 69 which extends from the rear side to the front side, the second fan 82 is placed above a side of the video processing board 69 in such a way that a side of the second fan 82 will coincide approximately with the side of the video processing board 69.

Furthermore, the third fan 83 provided on the rearmost side is intended to exhaust air from the second heat generating region b and third heat generating region c. The third fan 83, whose multiple blades 83a exhaust air through an opening 83b, is placed such that approximately 50% the surface area of the opening 83b will cover the second heat generating region b and that the remaining approximately 50% the surface area of the opening 83b will cover the third heat generating region c.

Thus, the first heat generating region a which causes the highest temperature rise corresponding to the amount of heat developed by electronic components driven, for example, at 130 W is ventilated forcibly by the first and second fans 81 and 82 at approximately 107%(=60%+47%) the ventilation capacity of each fan.

That is, the PCB unit 59 of the ultrasound imaging apparatus 3 has an interior cooling structure equipped with the first and second fans 81 and 82 to forcibly ventilate the DBF unit 67 containing the first heat generating region a which causes the highest temperature rise out of the three heat generating regions a, b, and c due to the highest total amount of power consumption of electronic components and thereby keep the air in the DBF unit 67 below the maximum ambient operating temperature of the electronic components.

On the other hand, the second heat generating region b which causes the second highest temperature rise corresponding to the amount of heat developed by electronic components driven, for example, at 56 W (=43 W+13 W) is ventilated forcibly by the first, second, and third fans 81, 82, and 83. Also, the third heat generating region c which causes the lowest temperature rise corresponding to the amount of heat developed by electronic components driven, for example, at 13 W is ventilated forcibly by the second and third fans 82 and 83.

Consequently, in the PCB unit 59 of the ultrasound imaging apparatus 3, the second heat generating region b and third heat generating region c are ventilated forcibly by the second and third fans 82 and 83 to keep the electronic components mounted on the control board 68, signal processing board 66, and video processing board 69 well below the maximum ambient operating temperature.

Since downsizing of entire external shape results in restricted inner space, the ultrasound imaging apparatus 3 according to the present embodiment configured as described above has an interior cooling structure which is configured such that multiple boards are arranged in stacks with the board which consumes the most power and becomes very hot being placed in the uppermost part to minimize thermal effect of the hot board on electronic components mounted on the other boards and that the three fans 81, 82, and 83 are positioned optimally to forcibly exhaust the heated air efficiently and thereby keep the interior of the ultrasound imaging apparatus 3 below the maximum ambient operating temperature.

As described above, the ultrasound imaging apparatus 3 according to the present embodiment is configured with the interior cooling structure which can reduce temperature rises inside the apparatus due to the heat developed by the electronic components mounted on multiple boards arranged in a small space of the apparatus resulting from downsizing and cool the apparatus efficiently below the maximum ambient operating temperature of the electronic components.

The present invention makes it possible to implement an interior cooling structure which can efficiently cool an interior of an apparatus heated by the electronic components mounted on multiple boards arranged in a small space of the apparatus resulting from downsizing as well as to implement an ultrasound imaging apparatus equipped with the interior cooling structure.

The invention described above by way of the embodiment is not limited to the embodiment and variations thereof. Numerous variations can be made at implementation levels without departing from the spirit of the present invention. Furthermore, the above embodiment includes inventions at various stages, and various inventions can result from proper combinations of multiple components disclosed herein.

For example, even if some of the components of the embodiment are removed, as long as the problems to be solved by the invention can be solved and the advantages of the invention are available, the resulting configuration can constitute an invention.

What is claimed is:
1. An interior cooling structure comprising:
 a frame in which a plurality of circuit board modules are stacked, with electronic components mounted on the plurality of circuit board modules by being classified by function;
 an external housing which covers the frame together with the plurality of circuit board modules;
 a plurality of cooling devices which reduce temperature rises in the external housing caused by heat produced by the plurality of circuit board modules; and a heat generating region partitioned in such away as to enclose a circuit board module which has the highest total power consumption out of the plurality of circuit board modules, wherein the plurality of cooling devices are arranged in such away as to reduce temperature rises in the heat generating region by displaying capacity higher than capacity of each of the cooling devices.

2. The interior cooling structure according to claim 1, wherein the circuit board module which has the highest total power consumption is placed in the uppermost part of the frame.

3. The interior cooling structure according to claim 1, further comprising another heat generating region partitioned so as to enclose a circuit board module different from the circuit board module which has the highest total power consumption, wherein temperature rises in the other heat generating region is also reduced by the plurality of cooling devices.

4. The interior cooling structure according to claim 2, further comprising another heat generating region partitioned so as to enclose a circuit board module different from the circuit board module which has the highest total power consumption, wherein temperature rises in the other heat generating region is also reduced by the plurality of cooling devices.

5. The interior cooling structure according to claim 1, wherein:

the plurality of cooling devices are three blowers with equal ventilation capacity; and the three blowers are installed side by side in a horizontal direction on a flank of the frame.

6. The interior cooling structure according to claim 2, wherein:

the plurality of cooling devices are three blowers with equal ventilation capacity; and the three blowers are installed side by side in a horizontal direction on a flank of the frame.

7. The interior cooling structure according to claim 3, wherein:

the plurality of cooling devices are three blowers with equal ventilation capacity; and the three blowers are installed side by side in a horizontal direction on a flank of the frame.

8. The interior cooling structure according to claim 5, wherein the three blowers are installed side by side with centers of rotation of multiple blades shifted stepwise vertically up or down.

9. The interior cooling structure according to claim 6, wherein the three blowers are installed side by side with centers of rotation of multiple blades shifted stepwise vertically up or down.

10. The interior cooling structure according to claim 7, wherein the three blowers are installed side by side with centers of rotation of multiple blades shifted stepwise vertically up or down.

11. The interior cooling structure according to claim 1, wherein the plurality of circuit board modules are provided with the heat generating regions partitioned by electromagnetic shielding material so as to enclose the plurality of circuit board modules.

12. The interior cooling structure according to claim 2, wherein the plurality of circuit board modules are provided with the heat generating regions partitioned by electromagnetic shielding material so as to enclose the plurality of circuit board modules.

13. The interior cooling structure according to claim 3, wherein the plurality of circuit board modules are provided with the heat generating regions partitioned by electromagnetic shielding material so as to enclose the plurality of circuit board modules.

14. The interior cooling structure according to claim 5, wherein the plurality of circuit board modules are provided with the heat generating regions partitioned by electromagnetic shielding material so as to enclose the plurality of circuit board modules.

15. The interior cooling structure according to claim 8, wherein the plurality of circuit board modules are provided with the heat generating regions partitioned by electromagnetic shielding material so as to enclose the plurality of circuit board modules.

16. An ultrasound imaging apparatus to which an ultrasound medical apparatus is detachably connected, the ultrasound imaging apparatus comprising:

an interior cooling structure including:

a frame in which a plurality of circuit board modules are stacked, with electronic components mounted on the plurality of circuit board modules by being classified by function;

an external housing which covers the frame together with the plurality of circuit board modules;

a plurality of cooling devices which reduce temperature rises in the external housing caused by heat produced by the plurality of circuit board modules; and a heat generating region partitioned in such away as to enclose a circuit board module which has the highest total power consumption out of the plurality of circuit board modules, wherein the plurality of cooling devices are arranged in the interior cooling structure in such away as to reduce temperature rises in the heat generating region by displaying capacity higher than capacity of each of the cooling devices.

17. The ultrasound imaging apparatus according to claim 16, wherein the circuit board module which has the highest total power consumption is placed in the uppermost part of the frame.

18. The ultrasound imaging apparatus according to claim 16, further comprising another heat generating region partitioned so as to enclose a circuit board module different from the circuit board module which has the highest total power consumption, wherein temperature rises in the other heat generating region is also reduced by the plurality of cooling devices.

19. The ultrasound imaging apparatus according to claim 16, wherein:

the plurality of cooling devices are three blowers with equal ventilation capacity; and the three blowers are installed side by side in a horizontal direction on a flank of the frame.

20. The ultrasound imaging apparatus according to claim 19, wherein the three blowers are installed side by side with centers of rotation of multiple blades shifted stepwise vertically up or down.

21. The ultrasound imaging apparatus according to claim 16, wherein the plurality of circuit board modules are provided with the heat generating regions partitioned by electromagnetic shielding material so as to enclose the plurality of circuit board modules.

* * * * *